(12) United States Patent
Papoutsakis et al.

(10) Patent No.: US 9,023,618 B2
(45) Date of Patent: May 5, 2015

(54) ENGINEERING COMPLEX MICROBIAL PHENOTYPES WITH TRANSCRIPTION ENHANCEMENT

(75) Inventors: Eleftherios T. Papoutsakis, Newark, DE (US); Stefan Marcus Gaida, Newark, DE (US)

(73) Assignee: Eleftherios Papoutsakis and Stefan Gaida, Newark, DE (US)

(*) Notice: Subject to any disclaimer, the term of this patent is extended or adjusted under 35 U.S.C. 154(b) by 776 days.

(21) Appl. No.: 13/151,909

(22) Filed: Jun. 2, 2011

(65) Prior Publication Data
US 2012/0035078 A1 Feb. 9, 2012

Related U.S. Application Data

(60) Provisional application No. 61/350,679, filed on Jun. 2, 2010, provisional application No. 61/484,474, filed on May 10, 2011.

(51) Int. Cl.
| | |
|---|---|
| C12P 21/06 | (2006.01) |
| C12P 21/04 | (2006.01) |
| C12N 15/70 | (2006.01) |
| C12N 15/10 | (2006.01) |
| C12N 1/36 | (2006.01) |
| C12N 9/12 | (2006.01) |
| C12R 1/01 | (2006.01) |

(52) U.S. Cl.
CPC . *C12N 15/70* (2013.01); *C12R 1/01* (2013.01); *C12N 15/1058* (2013.01); *C12N 1/36* (2013.01); *C12N 9/1247* (2013.01); *C12N 15/1079* (2013.01)

(58) Field of Classification Search
None
See application file for complete search history.

(56) References Cited

U.S. PATENT DOCUMENTS

2004/0209249 A1* 10/2004 Aevarsson et al. ............. 435/6
2009/0176659 A1*  7/2009 Stephanopoulos et al. .... 506/10

OTHER PUBLICATIONS

Ambrosi et al., Involvement of AlgQ in Transcriptional Regulation of Pyoverdine Genes in *Pseudomonas aeruginosa* PAO1, Journal of Bacteriology, Aug. 2005, p. 5097-5107.*
Sabree et al., Heterologous expression in the metagenomics era, Ph.D. Thesis, dated 2007, published by University of Wisconsin-Madison.*
Klein-Marcuschamer et al., *Applied Envir Microbiology* 75:2705-11 (2009).
Yan and Liao, *J Ind Microbiol Biotechnol* 36:471-79 (2009).
Yomano et al., *J Industrial Microbiology & Biotechnology* 20:132-38 (1998).
PCT/US2011/038921 International Search Report dated Feb. 21, 2012 by Jung Min Park Korean Intellectual Property Office.
Alper, H. and G. Stephanopoulos (2007). "Global transcription machinery engineering: a new approach for improving cellular phenotype." *Metab Eng* 9(3): 258-267.
Alsaker, et al. (2010). "Metabolite stress and tolerance in the production of biofuels and chemicals: Gene-expression-based systems analysis of butanol, butyrate and acetate stresses in the anaerobe *Clostridium acetobutylicum.*" *Biotechnol Bioeng* 105: 1131-1147.

(Continued)

*Primary Examiner* — Reza Ghafoorian
(74) *Attorney, Agent, or Firm* — RatnerPrestia (57) ABSTRACT

The present invention relates to a recombinant *E. coli* exhibiting a complex phenotype, comprising one or more RNA polymerase subunit genes, one or more functional genes, and, optionally, one or more transcription factors from a heterologous prokaryote. Also provided are methods for screening such a recombinant *E. coli*.

8 Claims, 9 Drawing Sheets

(56) References Cited

OTHER PUBLICATIONS

Blanco-Rosete, S. and C. Webb (2008). "Emerging biorefinery markets: global context and prospects for Latin America." *Biofuels Bioproducts & Biorefining-Biofpr* 2(4): 331-342.

Borden, et al. (2010). "A genomic-library based discovery of a novel, possibly synthetic, acid-tolerance mechanism in *Clostridiu/I7 acetobutylicu/I7* involving non-coding RNAs and ribosomal RNA processing. ." *Metabolic Engineering* DOI:10.1016/j.ymben.2009.12.004 (2010).

Borden, J. R. and E. T. Papoutsakis (2007). "Dynamics of genomic-library enrichment and identification of solvent tolerance genes for *Clostfidium acetobutylicum.*" *Applied and Environmental Microbiology* 73(9): 3061-3068.

Curtis, T. P. and W. T. Sloan (2005). "Microbiology. Exploring microbial diversity—a vast below." *Science* 309(5739): 1331-1333.

Demirbas, A. (2009). "Biorefineries: Current activities and future developments." *Energy Conversion and Management* 50(11): 2782-2801.

Dien, et al. (2003). "Bacteria engineered for fuel ethanol production: current status." *Appl Microbiol Biotechnol* 63(3): 258-266.

Epicentre® Biotechnologies (2006). "Copy Control Fosmid Library Production kit." *Epicentre® Cat. No. CCFOS110*.

Fernandes, et al. (2003). "Solvent tolerance in bacteria: role of efflux pumps and cross-resistance with antibiotics." *International journal of Antimicrobial Agents* 22(3): 211-216.

Gabor, et al. (2004). "Quantifying the accessibility of the metagenome by random expression cloning techniques." *Environmental Microbiology* 6(9): 879-886.

Gibbons, W. R. and S. R. Hughes (2009). "Integrated biorefineries with engineered microbes and high-value co-products for profitable biofuels production." In *Vitro Cellular & Developmental Biology—Plant* 45(3): 218-228.

Gill, et al. (2002). "Genome-wide screening for trait conferring genes using DNA microarrays." *Proceedings of the National Academy of Sciences of the United States of America* 99(10): 7033-7038.

Gross, et al, (1998). "The functional and regulatory roles of sigma factors in transcription." *Cold Spring Harbor Symposia on Quantitative Biology* 63: 141-155.

Gupta, et al. (2006). "A solvent tolerant isolate of *Enterobacter aerogenes.*" *Bioresource Technology* 97(1): 99-103.

Hosokawa, et al. (2002). "Streptomycin-resistant (rpsL) or rifampicinresistant (rpoB) mutation in *Pseudomonas putida* kH146-2 confers enhanced tolerance to organic chemicals." *Environmental Microbiology* 4(11): 703-712.

Ingram, et al. (1987). "Genetic-Engineering of Ethanol-Production in *Escherichia-coli.*" *Appl Environ Microbiol* 53(10): 2420-2425.

Isken, S. and J. A. M. de Bont (1998). "Bacteria tolerant to organic solvents." *Extremophiles* 2(3): 229-238.

KEGG database Bsu RpoD (2010). "Protein sequence homology search for *B. subtilis* RpoD." http://ssdb.genome.jp/ssdb-bin/ssdbmbest?orgmgene=bsu:BSU25200.

KEGG database Bsu SigB (2010). "Protein homology search for the *B. subtilis* SigB." http://ssdb.genome.jp/ssdb-bin/ssdbmbest?orgmgene=bsu:BSU04730.

KEGG database Eco RpoD (2010). "Protein sequence homology search for *E. coli* k12 R p o D protein." http://ssdb.genome.jp/ssdb-bin/ssdbmbest?orgmgene=eco:b3067.

Kim, et al. (1992). "Stable Propagation of Cosmid Sized Human DNA Inserts in an F-Factor Based Vector." *Nucleic Acids Research* 20(5): 1083-1085.

Leggewie, et al. (2006). "A novel transposon for functional expression of DNA libraries." *Journal of Biotechnology* 123(3): 281-287.

Martinez-Morlas, et al. (1999) "Chromosomal Integration of Heterologous DNA in *Escherichia coli* with Precise Removal of Markers and Replicons Used during Construction" Nov., *J Bacteriol* 181, 7143.

Nakamura, C. E. and G. M. Whited (2003). "Metabolic engineering for the microbial production of 1,3-propanediol." *Current Opinion in Biotechnology* 14(5): 454-459.

Neumann, et al. (2005). "Cells of *Pseudomonas putida* and *Enterobacter* sp adapt to toxic organic compunds by increasing their size." *Extremophiles* 9(2): 163-168.

Paredes, et al. (2005). "A comparative genomic view of clostridial sporulation and physiology." *Nature Reviews Microbiology* 3(12): 969-978.

Ragsdale, S. W. and E. Pierce (2008). "Acetogenesis and the Wood-Ljungdahl pathway of CO2 fixation." *Biochimica Et Biophysica Acta-Proteins and Proteomics* 1784(12): 1873-1898.

Ramos, et al. (2002). "Mechanisms of solvent tolerance in gram-negative bacteria." *Annual Review of Microbiology* 56: 743-768.

Ramos, et al. (1997). "Mechanisms for solvent tolerance ill bacteria." *Journal of Biological Chemistry* 272(7): 3887-3890.

Riesenfeld, et al. (2007). Methods for soil metagenomics: extraction and cloning of soil DNA. *Manual of environmental microbiology.* C. j. Hurst, Crawford, R. L., Garland, j. L., Lipson, D. A., Mills, A. L., Stetzenbach, L. D. Washington, D. C., ASM Press: 1063-1071.

Rondon, et al. (2000). "Cloning the soil metagenome: a strategy for accessing the genetic and functional diversity of uncultured microorganisms." *Appl Environ Microbiol* 66(6): 2541-2547.

Rude, M. A. and A. Schirmer (2009). "New microbial fuels: a biotech perspective." *Current Opinion in Microbiology* 12(3): 274-281.

Santos, et al. (2004). "Insights into *Pseudomonas putida* kT2440 response to phenol-induced stress by quantitative proteomics." *Proteomics* 4(9):2640-2652.

Schmeisser, et al. (2007). "Metagenomics, biotechnology with nonculturable microbes." *Applied Microbiology and Biotechnology* 75(5): 955-962.

Sorenson, M. k. and S. A. Darst (2006). "Disulfide cross-linking indicates that FlgMbound and free sigma(28) adopt similar conformations." *Proceedings of the National Academy of Sciences of the United States of America* 103(45): 16722-16727.

Stevens, M. J. A., D. Molenaar, et al. (2010). "Involvement of the Mannose Phosphotransferase System of *Lactobacillus plantarum* WCFS1 in Peroxide Stress Tolerance." Applied and environmental microbiology 76(11): 3748-3752.

Stevens, M. J. A., D. Molenaar, et al. (2010). "Sigma(54)-mediated control of the mannose phosphotransferase sytem in *Lactobacillus plantarum* impacts on carbohydrate metabolism." Microbiology—Sgm 156: 695-707.

Turnbaugh, P. J. and J. I. Gordon (2008). "An invitation to the marriage of metagenomics and metabolomics." *Cell* 134(5): 708-713.

Uchiyama, et al. (2005). "Substrate-induced gene-expression screening of environmental metagenome libraries for isolation of catabolic genes." *Nature Biotechnology* 23(1): 88-93.

Valdivia, R. H. and S. Falkow (1996). "Bacterial genetics by flow cytometry: Rapid isolation of *Salmonella typhimurium* acid-inducible promoters by differential fluorescence induction." *Molecular Microbiology* 22(2): 367-378.

Weisburg, et al. (1991). "16S ribosomal DNA amplification for phylogenetic study." *j Bacteriol* 173(2): 697-703.

Yazdani, S. S. and R. Gonzalez (2007). "Anaerobic fermentation of glycerol: a path to economic viability for the biofuels industry." *Current Opinion in Biotechnology* 18(3): 213-219.

Zheng, et al. (2008). "Commodity Chemicals Derived from Glycerol, an Important Biorefinery Feedstock." *Chemical Reviews* 108(12): 5253-5277. (This paper was withdrawn at the request of the Editor-in-Chief due to violations of the *Ethical Guidelines to Publication of Chemical Research* of the American Chemical Society).

\* cited by examiner

ENGINEERING COMPLEX MICROBIAL PHENOTYPES WITH TRANSCRIPTION ENHANCEMENT

CROSS-REFERENCE TO RELATED APPLICATION

This application claims the benefit of U.S. Provisional Application No. 61/350,679, filed Jun. 2, 2010, and U.S. Provisional Application No. 61/484,474, filed May 10, 2011, the contents of both of which are incorporated in their entireties.

REFERENCE TO U.S. GOVERNMENT SUPPORT

This work is supported by a grant from National Science Foundation (Award Nos. 0756451 and 1033926). The United States has certain rights in the invention.

FIELD OF THE INVENTION

The invention relates generally to engineering complex microbial phenotypes. In particular, the invention relates to recombinant microorganisms exhibiting a desirable complex phenotype as well as methods for engineering these recombinant microorganisms.

BACKGROUND OF THE INVENTION

Engineering of sturdy and tolerant process organisms has become an attractive goal for bioprocessing, including biorefinery. Typical bioprocess organisms, such as model organisms *Escherichia coli* (*E. coli*) and *Saccharomyces cerevisiae* (*S. cerevisiae*), are commonly used because of their extensive characterization as well as the availability of genetic toolboxes enabling easy genetic manipulation. Desirable phenotypes can be found in less characterized or unknown microorganisms (e.g., metagenomics), and will be beneficial if implemented or transferred into the model organisms to improve their bioprocessing characteristics. The desirable phenotype may be due to a known or unknown genotype.

Where the underlying genetics for a desirable phenotype are known, traditional metabolic engineering approaches can be used to transfer desirable traits from an organism to a model or production organism (e.g., *E. coli.*). As a result, expression of genes necessary for a desirable phenotype can be effectively achieved by hijacking the transcription machinery of a host organism by, for example, using host promoters as well as optimized ribosomal binding sites.

Where the underlying genotype for a desirable phenotype is not known and the desirable phenotype (e.g., tolerance) is complex, meaning that multiple genetic programs are involved, an effective screening mechanism needs to be employed first to elucidate the underlying genetics of the desired phenotype (e.g., screening of genomic libraries). It would be beneficial to employ the screening mechanism in a host organism for the implementation of the desired phenotype because this enables the finding of only important and functional parts of a potential wide span of genetic programs involved in the desired phenotype.

The basis for such a screening mechanism is generally functional expression of foreign genes in a host organism. In the circumstances of complex phenotypes, such a screening mechanism also enables identification of beneficial interactions among the foreign genes. Therefore, another limitation to be overcome is the number of foreign genes that can be screened in single cells, where they can potentially interact.

Common genetic elements employed for transfer of large heterologous DNA fragments into a host organism include fosmids and bacterial artificial chromosome's (BACs). Unfortunately, large heterologous DNA fragments in these genetic elements cannot be effectively employed to hijack the host transcription system by engineering strong promoters in front of the heterologous DNA fragments. The first transcriptional stop signal present in the heterologous DNA would lead to an end of transcription leaving all the genetic information located in genes behind this first stop signal un-transcribed. So, such genetic information would not be available for screening and, therefore, negate the benefits of having large genetic elements (e.g., BACs). The combinatorial space of interactions between the genes located in the large genetic elements (e.g., BACs) can only be exploited if the genes are expressed.

To date, there remains a need for a method to screen for microorganisms exhibiting a complex phenotype, which underlying genotype is not known.

SUMMARY OF THE INVENTION

The present invention relates to a recombinant *E. coli* exhibiting a complex phenotype and a method for screening such a recombinant *E. coli*.

A recombinant *E. coli* bacterium exhibiting a desirable complex phenotype is provided. The recombinant *E. coli* bacterium comprises one or more RNA polymerase subunit genes and one or more functional genes. The one or more RNA polymerase subunit genes and the one or more functional genes are expressed in the recombinant *E. coli* bacterium, and derived from a heterologous prokaryote.

The recombinant *E. coli* bacterium may further comprise one or more transcription factor genes. The one or more transcription factor genes are expressed in the recombinant *E. coli* bacterium, and derived from the heterologous prokaryote. The one or more transcription factor genes may be integrated into a chromosome of the recombinant *E. coli* bacterium.

The one or more RNA polymerase subunit genes may comprise an alpha, beta, beta', omega or sigma subunit gene. Preferably, the RNA polymerase subunit gene is a sigma subunit gene. Examples of the sigma subunit gene include rpoD, rpoN, sigH, rpoS, rpoE, sigB, sigF, sigE, and sigG. The one or more RNA polymerase subunit genes may be integrated into a chromosome of the recombinant *E. coli* bacterium.

The one or more functional genes may be integrated into a chromosome of the recombinant *E. coli* bacterium.

The complex phenotype may be tolerance to a toxic chemical, metabolite, substrate, high or low pH, oxidative stress, or bioprocess condition. The toxic chemical may be a solvent, carboxylic acid, hydrocarbon, phenolic compound, halogenated organic chemical, and toxic salt or metal ion. Preferably, the toxic chemical is ethanol, butanol or isopropanol.

The heterologous prokaryote may be in a genus selected from the group consisting of *Bacillus*, *Lactobacillus*, *Deinococcus*, *Clostridium*, *Actinomyces*, *Streptomyces*, *Pseudomonas*, *Escherichia*, *Rhodococcus*, and *Nocardioides*. Preferably, the heterologous prokaryote is *Lactobacillus plantarum*.

A method for screening a recombinant *E. coli* bacterium exhibiting a desirable complex phenotype is also provided. The method comprises expressing one or more RNA polymerase subunit genes and one or more functional genes in a host *E. coli* bacterium. The one or more RNA polymerase subunit genes and the one or more functional genes are derived from a heterologous prokaryote.

The method may further comprise expressing one or more transcription factor genes in the host *E. coli* bacterium. The one or more transcription factor genes are derived from the heterologous prokaryote. The one or more transcription factor genes are integrated into a chromosome of the recombinant *E. coli* bacterium.

The method may further comprise introducing the one or more functional genes into the host *E. coli* bacterium from one or more genomic libraries. The genomic libraries may be natural or enriched metagenomic libraries. The genomic libraries may also be generated from the heterologous prokaryote. The functional genes may be integrated into the chromosome of the host *E. coli* bacterium.

In the method according to the present invention, the one or more RNA polymerase subunit genes comprise a sigma subunit gene selected from the group consisting of rpoD, rpoN, sigH, rpoS, rpoE, sigB, sigF, sigE, and sigG. The one or more RNA polymerase subunit genes may be integrated into a chromosome of the recombinant *E. coli* bacterium.

BRIEF DESCRIPTION OF THE DRAWINGS

FIG. 1 shows the GFP-trap library approach. A) The destination vector contains the LR-cassette and a translational three-frame-stop signal (stop sign), with the sequence ATTG ATTAATT (underlined: stop codons) in front of the GFP gene, which has its own ribosomal binding site. A transcriptional terminator (cross) after the GFP gene ensures termination. The inducible lac operon ($P_{lac}$) promoter is to enable inducible transcription of library inserts using IPTG. The LR recombination cassette consists of a chloramphenicol resistance gene ($Cm_R$) and a ccdB gene flanked by AttR1 & AttR2 sites. Sheared Lpl genomic DNA is cloned into the entry pCR8/GW/Topo vector, which is surrounded by AttL1 and AttL2 sites. AttL1 and AttL2 sites (on the entry vector) allow for the recombination of the genomic DNA into the destination cassette removing the $Cm_R$ and ccdB on the GFP trap vector containing AttL1 and AttL2 sites, during the LR recombination reaction (catalyzed by the LR Clonase™ II Enzyme). B) The genomic library carrying vector after the LR-recombination. By incorporating a 3-frame-stop signal, translation of the GFP is not affected by the translation of the genomic fragment.

DETAILED DESCRIPTION OF THE INVENTION

The present invention is based on the discovery of a method for enhancement of heterologous gene expression in *E. coli* by engineering the host transcription machinery such that the engineered *E. coli* exhibits a desirable complex phenotype. In particular, RNA polymerase subunit genes, functional genes, and, optionally, transcription factor genes from a heterologous prokaryote are expressed in the *E. coli*.

According to one aspect of the present invention, a recombinant microorganism exhibiting a desirable phenotype is provided. The microorganism comprises one or more (e.g., one, two, three, four, five or more) RNA polymerase subunit genes and one or more (e.g., one, two, three, four, five or more) functional genes. The RNA polymerase subunit genes and the functional genes are expressed in the microorganism, and are derived from one or more (e.g., one, two, three, four, five or more) heterologous prokaryotes.

The recombinant microorganism may be a bacterium, yeast or more broadly fungus. Examples of the bacteria include Gram negative and Gram positive bacteria, for example, microorganisms of the genera *Clostridium, Bacillus, Lactobacillus, Radiococcus, Eschericiae, Listeria*, and *Stephylococcus*. Preferably, the microorganism is *E. coli*. The fungus may be in the genera *Saccharomyces, Klyveromyces, Pichia*, or *Sterigmatomyces*.

The heterologous prokaryote may be any prokaryote that is different from the microorganism. The heterologous prokaryote may be in a genus of *Bacillus, Lactobacillus, Deinococcus, Clostridium, Actinomyces, Streptomyces, Pseudomonas, Escherichia, Rhodococcus*, or *Nocardioides*. For example, the heterologous prokaryote may be *Lactobacillus plantarum* or *Lactobacillus bravis*, preferably *Lactobacillus plantarum*. The heterologous prokaryote may preferably exhibit the desirable phenotype.

The RNA polymerase subunit gene may encode an alpha, beta, beta', omega or sigma subunit. The sigma subunit may be rpoD, rpoN, sigH, rpoS, rpoE, sigB, sigF, sigE, or sigG. The RNA polymerase subunit genes may be present in one or more plasmids or integrated into one or more chromosomes of the microorganism (e.g., *E. coli*). Preferably, the RNA polymerase subunit genes are integrated into one chromosome of the microorganism. More preferably, the RNA polymerase subunit genes are integrated into the chromosome of E. coli.

The functional genes may be a metagenomic or synthetic DNA. The functional genes may be present in one or more plasmids, fosmids, BAC's or integrated into one or more chromosomes of the microorganism (e.g., E. coli). Preferably, the functional genes are integrated into one chromosome of the microorganism. More preferably, the functional genes are integrated into the chromosome of E. coli.

The microorganism may further comprise one or more (e.g., one, two, three, four, five or more) transcription factor genes. The transcription genes are expressed in the microorganism, and are derived from a heterologous prokaryote. The transcription factors may be responsible for general or specialized stress responses, starvation, and quorum sensing. The transcription factor genes may be present in one or more plasmids or integrated into one or more chromosomes of the microorganism (e.g., E. coli). Preferably, the transcriptional factor genes are integrated into one chromosome of the microorganism. More preferably, the transcriptional factor genes are integrated into the chromosome of E. coli.

The phenotype may be simple or complex. Preferably, the phenotype is complex. A simple phenotype refers to a phenotype modulated by a single functional gene while a complex phenotype refers to a phenotype modulated by two or more (e.g., two, three, four, five or more) functional genes. In general, a complex phenotype may involve multiple cellular structures and mechanisms, for example, membrane integrity, cell wall composition, synthesizing molecular pumps, alternating energy metabolism as well as other unknown mechanisms. Multiple genes and their interactions constitute the genetic basis of complex phenotypes.

Examples of complex phenotypes include tolerance to a toxic chemical, metabolite, substrate, high or low pH, oxidative stress, and/or bioprocess condition, and temperature sensitivity. A toxic chemical may be present in feedstock. It may also be a toxic side product, or an end product produced during a bioprocess or fermentation. Examples of toxic chemicals include a solvent, carboxylic acid, hydrocarbon, phenolic compound, halogenated organic chemical, and toxic salt or metal ion. Preferably, the toxic chemical is ethanol, butanol or isopropanol. The toxic chemicals may be useful for industrial applications, biofuel applications, and applications in industrial biocatalysis or bioremediation.

To identify and screen for multiple genes and their interactions, a novel method has been developed, namely a multilibrary approach (based on library enrichment). The basis of this strategy is that genes involved in a complex phenotype (e.g., ethanol tolerance) may be located in such libraries and could be used to enhance the phenotype in a microorganism if expressed. Through this advantage, cells containing beneficial genes can be enriched under stress, e.g., in ethanol stressed cultures, and identified through library plasmid sequencing. To ensure that genes, located distally in the genome, are present and interact in the same cells, multiple libraries are incorporated into a single host cell. The number of genes present in one library is limited by the size of its inserts. By using more than one library, combinations of inserts are possible and distant genes can be brought together in a single host cell.

Some of the most ethanol tolerant microorganisms besides S. cerevisiae are Lactobacilli, whereby minimal inhibitory concentrations of over 20% ethanol were observed for Lactobacillus plantarum. The multilibrary approach may be applied to identify functional genes involved in this superior ethanol tolerance, and the identified functional genes may be used to enhance the tolerance of a host E. coli. However, this can only be accomplished if L. plantarum genes are functionally expressed in the host E. coli.

The expression of genes in prokaryotes is highly controlled at the level of transcription and lack of transcription due to the inability of the host transcription machinery to recognize necessary transcription initiation signals, like promoters, is a problem encountered in heterologous gene expression. Expression of multiple heterologous genes is necessary for engineering a complex phenotype while common expression systems are not useful for this purpose. Novel methods have been developed to successfully apply the multilibrary approach towards the engineering of complex phenotypes.

According to another aspect of the present invention, a method for screening a recombinant microorganism exhibiting a desirable phenotype is provided. The method comprises expressing one or more (e.g., one, two, three, four, five or more) RNA polymerase subunit genes and one or more (e.g., one, two, three, four, five or more) functional genes in a host microorganism, and the RNA polymerase subunit genes and the functional genes are derived from a heterologous prokaryote.

The method may further comprise expressing one or more (e.g., one, two, three, four, five or more) transcription factor genes in the host microorganism. The transcription factor genes are derived from the heterologous prokaryote.

The method may also further comprise introducing the functional genes into the host microorganism from one or more genomic libraries. The genomic library may be a natural or enriched metagenomic library. It may be generated from the heterologous prokaryote. Such a library contains potentially beneficial inserts for selecting beneficial cellular phenotypes or desirable phenotype.

The host microorganism may be a bacterium, yeast or more broadly fungus. The bacterium may be Gram negative or Gram positive. Examples of the bacterium include microorganisms of the genera Clostridium, Bacillus, Lactobacillus, Radiococcus, Eschericiae, Listeria, and Stephylococcus. Preferably, the microorganism is E. coli. The fungus may be in the genera Saccharomyces, Klyveromyces, Pichia, or Sterigmatomyces.

In accordance with the present invention, upon expression of heterologous functional genes, heterologous RNA polymerase subunit genes, and, optionally, heterologous transcription factor genes in a host microorganism (e.g., E. coli), the host microorganism acquires a desirable phenotype, simple or complex. Heterologous functional genes contributing to the desirable phenotype in the recombinant microorganism may be identified by sequencing the heterologous functional genes present in the recombinant microorganism. Such identified functional genes may be introduced into other microorganisms to improve or introduce the desirable phenotype in the other microorganisms.

The methods in accordance with the present invention may be used to identify and generate recombinant microorganisms (e.g., E. coli) that have novel catabolic capabilities, such as the ability to degrade cellulose or xylan or other complex carbon sources.

The methods in accordance with the present invention may also be used to identify and generate recombinant microorganisms (e.g., E. coli) that have novel anabolic capabilities, such as the ability to produce any desirable chemical or compound, by identifying either previously unknown pathways for the specific chemical or by identifying limiting enzymatic steps for the production of the chemical.

Transcription of genes is achieved by a RNA-polymerase, which is a multienzyme complex composed of several subunits. Transcription itself is a highly controlled process using a complex regulation system composed of cis factors, DNA sequences like promoters and interacting trans factors, like sigma subunits. The interaction of these factors is necessary for the start of transcription. Different sigma factors recognize different promoters and therefore regulate differential expression of a genome.

Heterologous genes can only be transcribed if the host transcription machinery, including, for example, sigma factors, recognizes the heterologous promoters. The idea of enhancing the transcription of heterologous genes in a particular host organism is to express several heterologous sigma factors to increase the variety of promoters recognized by the host transcription machinery.

For example, the expression of *Lactobacillus plantarum* (Lpl) genes in a host *E. coli* can be enhanced. Three major sigma factors of Lpl, namely rpoD, rpoN and sigH, can be expressed in *E. coli*, and their effects on the transcription of Lpl genes can be exploited. Green fluorescence from a genomic Lpl GFP-trap library in conjunction with a high-through put flow cytometry assay can be used as a measurement of the degree of transcription of Lpl genes in *E. coli*.

By expressing Lpl sigma factors in *E. coli*, the transcription of Lpl genes, measured as green fluorescence, can be enhanced. Two compatible plasmids may be used, one vector for the expression of the Lpl sigma factor and another one for the genomic Lpl GFP-trap library. This system may be used to elucidate whether the incorporation of Lpl genes and heterologous sigma factors into a host cell will lead to an enhancement of transcription of the Lpl genes. Upon successful demonstration, these sigma factors may be implemented into a genome to engineer suitable screening hosts. These hosts can then be used to screen large genomic libraries like fosmid and BAC based genomic or metagenomic libraries.

The host machinery can be augmented with heterologous sigma factors, which recognize specific promoter sequences of heterologous genes, and therefore enable effective transcription initiation leading to functional expression of the heterologous genes.

EXAMPLE 1

Expression of Lpl Sigma Factors in *E. coli*

The Lpl sigma factors sigH, rpoD as well as rpoN will be expressed from a low copy number plasmid with the p15A origin of replication under the control of the inducible lac promoter. The gene product of lacI can effectively repress the lac promoter. The commercially available expression vector pACYC-Duet from Novogen carries a copy of lacI and has a p15A origin of replication. This expression vector is optimized for protein expression driven by the T7 system. So, the expression vector carries two multiple cloning sites (MCS), which are under the control of the T7-lac promoter, a hybrid promoter of the T7 promoter and the repressor binding site of the lac promoter. This strong expression system is not suitable for expressing the Lpl sigma factors, because the protein amount from genes expressed under the control of the T7 expression system can reach very high concentrations in *E. coli* leading to the formation of inclusion bodies with non-functional proteins. Therefore, the expression vector was genetically modified to allow the expression of the sigma factors driven by the *E. coli* RNA-polymerase under the control of the inducible lac promoter.

The new expression vector was constructed in the following fashion. pACYC-DUET was used as a template in a PCR to amplify the p15A origin, the lacI and the chloramphenicol resistance gene. In another PCR, a LR-cassette was amplified. All PCR amplifications were performed with the high fidelity DNA polymerase Phusion, NEB biolabs, to avoid mutations due to amplification errors. After phosphorylation of the LR-cassette PCR product with T4-DNA-ligase, NEB, an in vitro ligation with Quick Ligase, NEB, was used to fuse this product with the pACYC-Duet PCR product. The resulting vector was transformed into chemically competent cells (One Shot® ccdB Survival™ cells, Invitrogen) and isolated from the transformed cells on chloramphenicol LB plates. The correct insertion of the LRcassette was verified by restriction digests and sequencing.

The LR-cassette was introduced to create an expression destination vector, named pACYC-LR, for in vitro LR recombination reactions enabling an effective way to introduce multiple sigma factors in the expression destination vector.

Lpl sigma factors were PCR amplified from gDNA of Lpl and introduced by restriction cloning into the MCS of the pUC19 vector. Correct insertion was verified by restriction digest. The pUC19 MCS is located after a repressible lac promoter, which can be used to transcribe the sigma factors with the native *E. coli* RNA polymerase. pUC19 has a high copy number in cells due to its colE origin of replication, which would translate to a high gene dosage if the sigma factors would be expressed from this construct. Such a high gene dosage of a regulatory acting protein could potentially be interfering with the control of the native transcription of the host organism. To avoid this potential problem, the sigma factors augmented with the lac promoter were amplified again via PCR and cloned via TOPO-TA cloning into the commercial entry vector pCR8/GW/TOPO, Invitrogen. All cloning steps of the sigma factors so far were performed in NEB-5-alpha cells, which carry an F-plasmid with a lacI$^q$, in order to repress the expression of the sigma factors. The sigma factors located in the entry vector were transferred via an in vitro LR recombination into the expression destination vector pACYC-LR. Depending on the cloned sigma factors, the final constructs were named pACYC-"name of sigma factor" (e.g., pACYC-sigH). Because of the lacI copy present in the vector, these constructs effectively repress themselves the expression of the sigma factors and were transformed in NEB-10-beta cells, which do not process additional vectors.

The expression of sigma factors in *E. coli* was verified by qRT-PCR on the pACYC-sigH construct. A pACYC-sigH culture was grown out to an OD of about 0.5 and split into three aliquots. The expression of sigH was induced in one aliquot with 1 mM IPTG and another one with 0.5 mM IPTG. The leftover aliquot served as the noninduced control. RNA samples were taken 10, 30 and 60 min after induction and cell pellets were stored at −85° C. until RNA extraction. The RNA extraction was performed with an RNeasy kit, Qiagen, following the manufacturer's instruction. 2 μg of RNA were reverse transcribed with a High Capacity cDNA Reverse Transcription kit, Applied Biosystems. In a next step, this cDNA was used in a qRT-PCR employing sigH specific primers and SYBR Green PCR Master Mix, Applied Biosystems, following the manufacturer's recommendations. As a negative control, cDNA from a RNA extraction from NEB-10-beta cells without pACYC-sigH was used. As positive controls, the 16s RNA of *E. coli* was used. The measured ct-values can be found as mean values from 3 (technical) replicates in Table 1.

TABLE 1

Mean Ct-values for the expression of L. plantarum sigma factor sigH in E. coli.

| | control (0 mM IPTG) | | | 0.5 mM IPTG | | |
|---|---|---|---|---|---|---|
| | 16s | sigH | RNA | 16s | sigH | RNA |
| 10 min | 04.38 ± 0.167 | 22.07 ± 0.072 | 25.70 ± 0.353 | 04.48 ± 0.046 | 14.41 ± 0.145 | 24.99 ± 0.224 |
| 30 min | 04.70 ± 0.171 | 21.62 ± 0.109 | 23.84 ± 0.271 | 04.55 ± 0.103 | 14.22 ± 0.022 | 24.50 ± 0.213 |
| 60 min | 04.47 ± 0.181 | 19.24 ± 0.114 | 21.37 ± 0.052 | 04.48 ± 0.085 | 14.37 ± 0.275 | 23.81 ± 0.200 |

| | 1 mM IPTG | | |
|---|---|---|---|
| | 16s | sigH | RNA |
| 10 min | 04.73 ± 0.242 | 14.96 ± 0.154 | 24.19 ± 0.23 |
| 30 min | 04.77 ± 0.313 | 14.39 ± 0.115 | 25.23 ± 0.27 |
| 60 min | 05.22 ± 0.360 | 14.92 ± 0.143 | 24.46 ± 0.23 |

| Negative control (NEB-10-beta cells) | | | Non template control (H20) | |
|---|---|---|---|---|
| 16s | sigH | RNA | 16s | sigH |
| 05.28 ± 0.48 | 33.91 ± 0.282 | 34.41 ± 0.65 | 29.95 ± 1.212 | 35.19 ± 0.816 |

In Table 1, expression of sigH was detected in cultures induced with IPTG. Mean Ct-values between 14 and 15 were observed for both concentration levels (0.5 and 1 mM IPTG) and for all sampling time points (10 min, 20 min and 30 min). Samples from a non-induced culture (control, 0 mM IPTG) showed Ct-values of 19.2 to 22, indicating a good repression of the transcription of sigH. As a control for a functional assay, primers against the 16s RNA of E. coli, which is always present, were used leading to low Ct-values for a functional assay (shown in the row labeled as 16s). RNA samples were loaded to confirm that the observed Ct-values for the expression of sigH is not due to plasmid contamination of the cDNA. The specificity of the sigH Q-RT-PCR primer set was tested by loading cDNA generated from an RNA extraction of cells, which do not contain the expression vector (shown as "negative control (NEB-10-beta cells)." A standard non-template control was performed by loading $H_2O$ to each mastermix instead of cDNA (containing 16s or sigH primer mix). All Ct-values are given in the format mean±standard deviation, based on a total of n=3 replicates performed. In view of the observed ct-values, sigH can be expressed in E. coli and that the repression system of the pACYC-based expression destination vector works.

EXAMPLE 2

Construction of L. plantarum GFP-Trap Libraries

Figure 1:
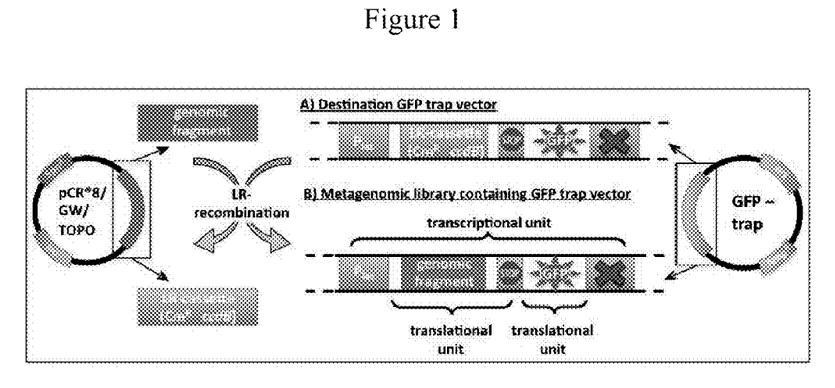

Metagenomic or single species GFP-trap libraries can be constructed by placing GFP expression under the control of promoters from the library inserts, whereby GFP is not expressed as a fusion protein. The library construct that enables this technology is shown in FIG. 1 and is discussed in detail below (the $P_{lac}$ promoter shown in FIG. 1 will not be normally used as explained below).

The microbial library is then cultivated in a host strain under any chosen conditions, and analyzed by Flow Cytometry (FC) for GFP expression (by GFP-specific fluorescence). If a (heterologous) promoter placed in front of the GFP gene in the GFP trap construct is recognized by E. coli, then GFP fluorescence will be detected; otherwise not. Thus, for library inserts containing a heterologous promoter in the correct orientation (FIG. 1) and assuming no $P_{lac}$ is present or active, one can examine if the promoter is recognized by E. coli.

An Lpl genomic GFP-trap library was constructed, with average size inserts of 900 bps. The preliminary data collected further support the findings that E. coli recognizes a very small fraction of heterologous promoters from Lpl. This library, A1LpSg, was shuffled to a destination vector (pUC-LR-GFP) via the LR recombination reaction. The destination vector was constructed by using a pUC19 backbone, and contains a destination cassette, a GFP coding gene, and the inducible lac promoter ($P_{lac}$) in front of the recombination cassette. By incorporating a translational stop signal after the recombination site, the translation of any transcript originating from the transcription of the library insert is effectively stopped and does not influence the translation of the GFP protein. So, the GFP open reading frame constitutes its own translational unit and was augmented with an optimized ribosomal binding site (RBS) for optimal translation (FIG. 1). In this library, the $P_{lac}$ was used to test whether a large fraction of the library containing cells fluoresce due to GFP expression can be made. Ideally, there is no expression of the library inserts from this promoter in the uninduced state (i.e., in the presence of active repressor (LacI)). However, like most promoters, $P_{lac}$ is leaky, and thus small levels of GFP would be expressed and after several generations (doubling time of the E. coli library containing cells is ca. 90-100 min), GFP expression will be detected due to this leakiness, and this is what was observed (see FIG. 4). Thus, GFP fluorescence is reliable as a metric of heterologous promoter recognition for only the first 4-6 library doublings after inoculation.

To obtain some preliminary results, this library was transformed into NEB 5-alpha F' I$^q$ E. coli cells in order to repress transcription from $P_{lac}$ prior to induction. The library culture was grown to an $OD_{600}$ of 0.5 (about 5 doublings after inoculation) and split into two aliquots. One aliquot was used as the uninduced control, and the other was induced with 1 mM IPTG. GFP expression was measured by FC. At the time of induction ($OD_{600}$ of 0.5), the uninduced culture should have expressed the GFP for all fragments containing Lpl promoters (in the correct orientation in front of the GFP gene) that are recognized by E. coli. The number of clones expressing GFP at that point was less than 2%.

A preliminary model was developed to estimate the fraction of library inserts which are likely to carry a promoter-containing interoperon (IO) region (non-coding DNA between operons). The chromosome size of Lpl is 3,308,274 bps, the % of non-coding DNA is 17%, the number of operons is 1,893, and 98% of the IO distances are less than 900 bps. For a library insert size of 900 bps, the probability that a library fragment contains an entire IO region is 17% (coincidentally the same as the fraction of non-coding genomic DNA; if the library insert size is increased to 1,500 bps, this fraction becomes 33%). In reality, a larger fraction of inserts will contain an Lpl promoter because promoters have a location bias near the start codon of the first ORF of an operon. So, 17% is a conservative number. The real number is more like 20-25% for the 900 bp fragment size. Because in this library a fragment can be inserted in one of two orientations, but most promoters are unidirectional, half of the 17% (or 20-25%) of the inserts would contain an Lpl promoter (i.e., 8 to 12% of the library clones) that can be detected by GFP fluorescence. 2% is a low fraction of Lpl promoter recognition.

Figure 2:
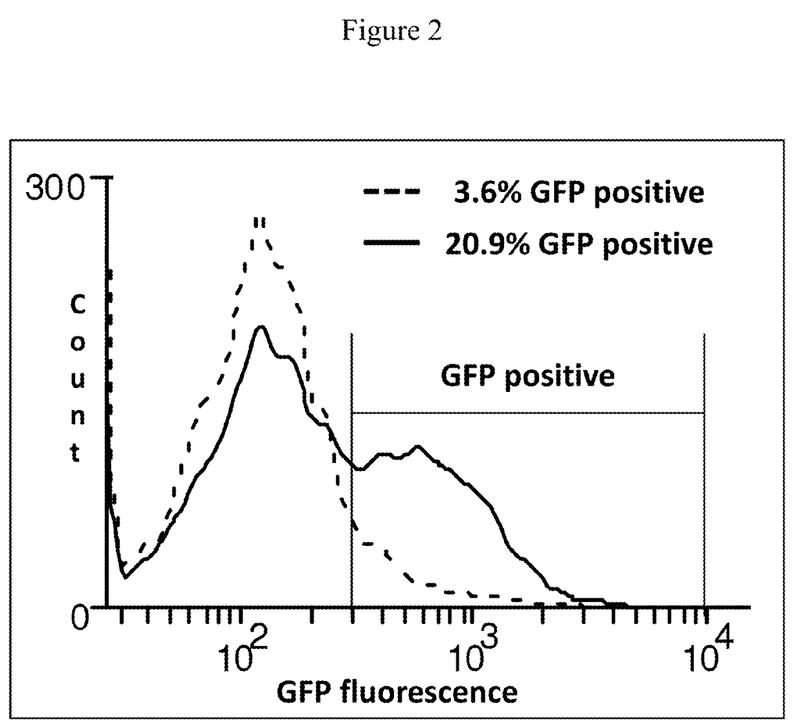
FIG. 2 shows GFP expression of GFP-trap Lpl library with an inducible lac promoter in a non-induced culture (dashed line) and an induced culture (solid line) at 120 min post induction with IPTG. The GFP expression profile of the non-induced culture is overlaid with that of the induced culture.

For positive controls, the GFP fluorescence was checked after induction for up to 360 min. As expected from the 90-100 min doubling time, it was found that GFP fluorescence increases dramatically at ca. 120 min post induction, with ca. 21% (this increases to 35% at 360 mins, which is <4 doublings past induction) of cells showing GFP expression (vs. 3.6% of the uninduced; FIG. 2). The 3.6% at 120 min now contains cells that fluoresce due to $P_{lac}$ leakiness in view of the good stability of the GFP protein. The presence of transcriptional terminators and other mRNA stability and secondary structures prevents the expression of GFP in all induced cells containing a GFP-trap library insert.

Figure 3:
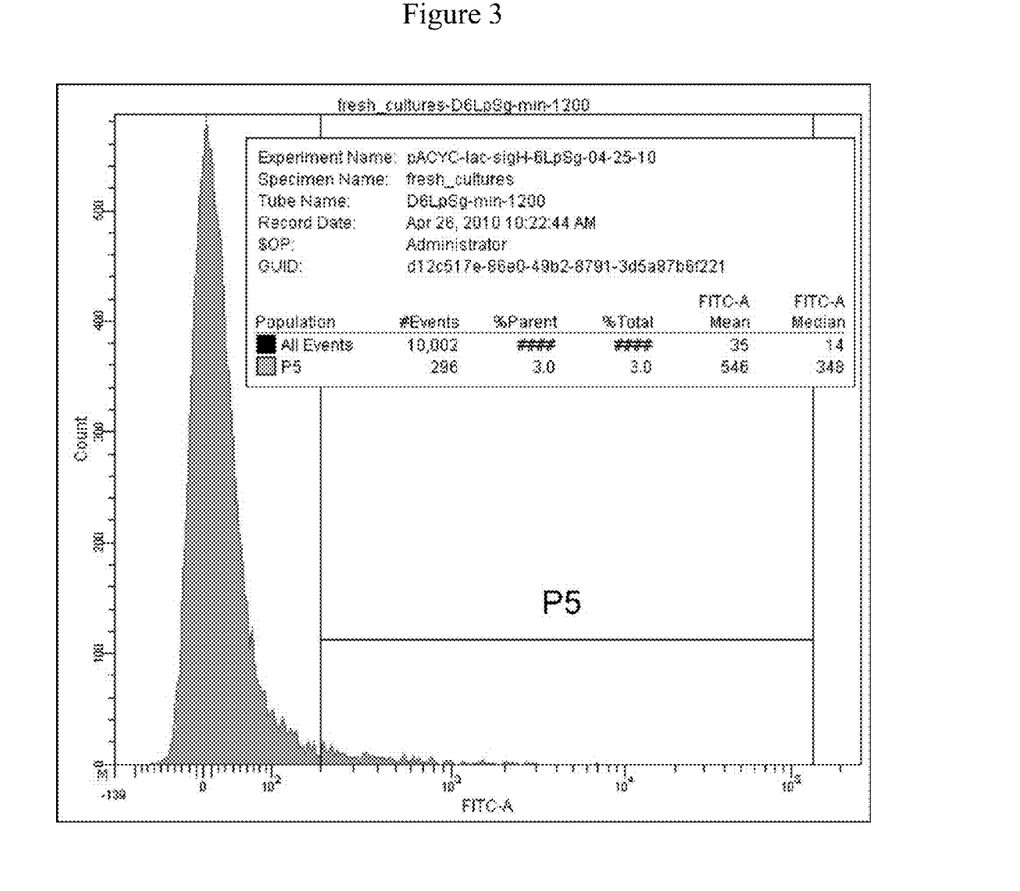
FIG. 3 shows GFP expression of the D6LpSg library after 1,200 min cultivation. GFP positive cells are located in the shown gate (P5); a total of 3% of cells were found in this gate.

In order to avoid the leakiness of the $P_{lac}$ promoter in front of the GFP-trap library and to enable the use of this repression system ($P_{lac}$ and LacI) for the expression of the sigma factors, another promoter-less genomic Lpl GFP-trap library was constructed, namely D6LpSg. Again, library A1LpSg was shuffled to a destination vector via the LR recombination reaction (see FIG. 1 for details), but this time the destination vector, namely pLR-GFP, did not contain the $P_{lac}$ promoter. The library, D6LpSg, was checked for GFP expression over an extensive time period of 1,200 min and a maximum of 3% GFP expression could be observed (FIG. 3).

The examination of GFP expression for the D6LpSg library resulted in a low GFP expression, verifying that *E. coli* recognizes only a small number of Lpl promoters and that this new library can be used as a reporter system in conjunction with the expression of the Lpl sigma factors.

EXAMPLE 3

Transcription Enhancement of *L. plantarum* Genes in the Host *E. coli* Through the Expression of *L. plantarum* Sigma Factor rpoD The expression vector pACYC-rpoD has a p15A origin of replication and is therefore compatible with plasmids carrying the colE origin, like the genomic Lpl GFP-trap library D6LpSg. Both plasmids can be stably maintained in the same cell. The expression of rpoD can be induced from the repressed $P_{lac}$ through IPTG. Furthermore, this sigma factor can act on Lpl promoters located in the heterologous DNA inserts of the genomic Lpl GFP-trap libraries leading to GFP expression. The fluorescence of the GFP is measured with a flow cytometry in order to quantify the effect of the expressed heterologous sigma factor on the initiation of transcription of the heterologous genes.

Figure 4:
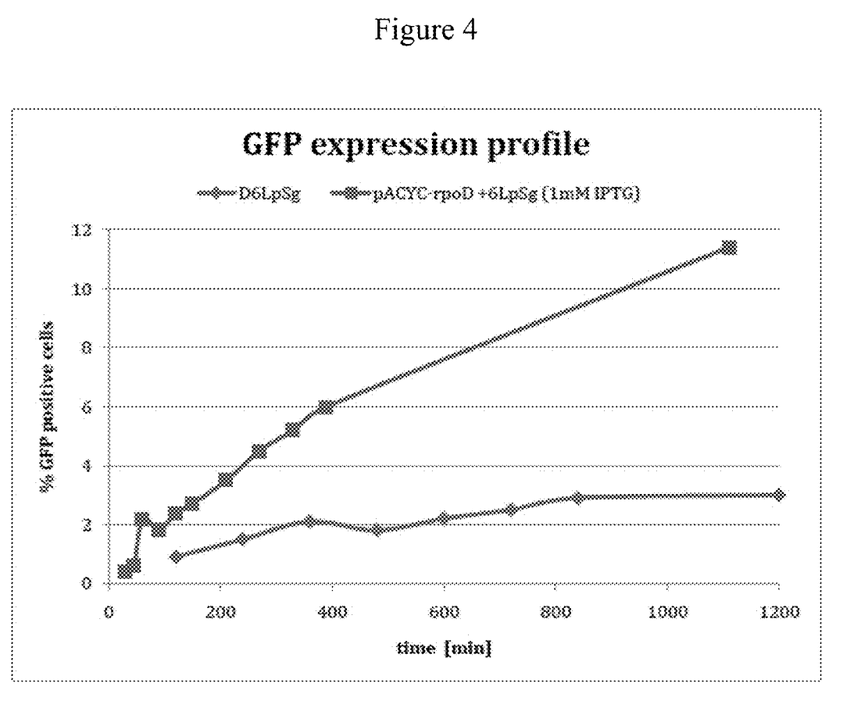
FIG. 4 shows GFP expression profiles of the genomic Lpl GFP trap library with ( ) and without ( ) the expression of the Lpl sigma factor rpoD. The GFP positive population was gated as shown in FIG. 3.

*E. coli* cells (NEB-10-beta cells) containing the pACYC-rpoD construct were made electrocompetent and transformed with the D6LpSg library per electroporation. 100 ng of D6LpSg plasmid was used per transformation, and a total of 10 electroporations were performed. The transformed cells were first outgrown in SOC at 37° C. for one hour before transferring into 250 ml LB containing 100 µg/ml ampicillin and 35 µg/ml chloramphenicol. Dilution series were plated on LB plates containing the same antibiotics to determine the size of the library. The size of the D6LpSg library combined with the pACYC-rpoD construct was $2.6 \times 10^8$ clones. After an outgrowth of 12 hours the culture reached an optical density of about 1.6. 2×5 ml was used to inoculate two 250 ml LB cultures containing again both antibiotics. The rest of the outgrown library was stored in 15% glycerol LB at −85° C. The two 250 ml cultures were outgrown to an optical density of 0.4. At this point one culture was induced with 1 mM IPTG to initiate the expression of rpoD. Flow samples along with optical density measurements were taken rigorously over a time course of 390 min. Flow samples were prepared by taking 0.5 ml culture suspension, washing them twice in 0.5 ml 1% NaCl and then diluting 1 to 3 µl of the washed cells in 1 ml 1% NaCl. A maximum of 11.4% of GFP positive cells could be detected for the induced (1 mM IPTG) culture containing the pACYC-rpoD construct and the D6LpSg library (FIG. 4).

EXAMPLE 4

Engineering *E. coli* to have a Transcriptional Machinery Capable of Utilizing a Large Fraction of Promoters from General and Specialized Metagenomic Libraries Nature harbors a huge genetic diversity, with an estimated $10^{30}$ microbes in the environment and an estimated $10^{16}$ prokaryotes per ton of soil. Microbial communities are phenotypically and genotypically diverse, and have evolved to survive diverse environments. Such microorganisms can provide the genetic material for identifying novel genes with functions related to the community niche, such as growth in heavily polluted regions. However, most organisms in the environment cannot be readily cultured and their communities cannot be reproduced in the laboratory. Metagenomic libraries aim to circumvent the necessity for cultivating entire microbial communities, and can be used to identify genes and genetic loci that can impart desirable traits such as more tolerant phenotypes or catabolic characteristics. The use of such genes and loci in the constructions of strains is useful for the production of chemicals and biofuels from biomass feedstocks, as well as for bioremediation. For example, soil could be treated with increasing concentrations of ethanol or butanol to enrich for microorganisms tolerant to these stressors, and then used to construct a metagenomic library in order to identify the genetic loci that impart such tolerance. However, such libraries need to be expressed in a desirable industrial host such as *E. coli*, and so the metagenomic-library DNA must be effectively recognized by the transcriptional machinery of the host.

While it is not practical to express in *E. coli* all sigma factors from all types of organisms that might be represented in a metagenomic library, it is still possible to express a larger fraction of genes from metagenomic libraries by expressing a few sigma factors from key prokaryotic phyla or genera. This is based on the fact that the primary sigma factor (SigA or RpoD; sigma 70 family) of the RNAP is very well preserved within phyla and/or genera. For example, the amino acid sequence of the *E. coli* RpoD is very well preserved among a very large number of Gram⁻ bacteria (KEGG database Eco RpoD 2010). Similarly, the *Bacillus subtilis* (*B. subtilis*) RpoD is very well preserved among many Gram⁺ prokaryotes (KEGG database Bsu RpoD 2010), but not nearly as well between *E. coli* and *B. subtilis*. One may be eventually able to design a transcriptional machinery that could express specialized classes of genes to attend to a desirable need or application. Many prokaryotes contain specialized sigma factors to attend to needs or survival under various environmental conditions or niches. For example, among *Firmicutes, bacilli* contain a stress-specific sigma factor (SigB; sigma 70 family), which is very well preserved among many Gram$^+$ bacteria, and notably other *Firmicutes* (e.g., *Listeria, Stephylococcus*) that contain such a sigma factor (KEGG database Bsu SigB 2010). By expressing the ropD and sigB genes from *B. subtilis* in *E. coli*, it will enable the expression of a larger fraction of metagenomic-library promoters, and especially from a metagenomic library that has been generated from samples that have been enriched for cells under chemical stress. A metagenomic library may be generated from soil stressed over a period of 3-4 months by addition of ethanol or butanol, which is enriched with organisms that are more tolerant to these two chemical stressants by expressing genes possibly regulated by SigB-like sigma factors. *Bacilli* and generally *Firmicutes* include a large number of soil organisms, and are thus likely to be enriched in the treated soils samples and metagenomic libraries. Other specialized sigma factors (e.g., SigF, SigE, and SigG) are engaged to regulate endospore formation in sporulating prokaryotes such as *bacilli* and *clostridia*. Thus, one may desire to express different classes of sigma factors in *E. coli* in order to select and express genes from metagenomic libraries that respond to specialized sigma factors. Many *firmicute* (and notably *bacillus* and *clostridial*) sigma factors have been easily and successfully expressed in *E. coli*.

Soil samples taken from rich garden soil may be enriched for aerobic, microaerobic and anaerobic organisms that can tolerate higher levels of ethanol and butanol by treating soil samples with these chemical stressants (control: untreated soil samples). Metagenomic promoter libraries (mpl) with a GFP trap may be constructed (as discussed above) to assess the fraction of promoters that is expressed in different *E. coli* strains. Three such libraries may be constructed: one from samples treated with ethanol (mplE library), one from samples treated with butanol (mplB library), and one from the control untreated samples (mplC library).

Ethanol is produced by many organisms in the environment and thus genetic systems have likely evolved widely for response and tolerance to this stressant. Butanol is also produced by some microbes (and notably clostridia) and is also catabolized by other microbes (e.g., by acetogens like *Moorella thermoacetica*, but the number of microbes that have specialized genetic systems to respond and tolerate this stressant is likely smaller. So, different microcosms will be enriched in soil treatment experiments; thus, if the strategy works with both libraries (and the control library), it is likely generalizable. Next, these three mpl libraries will be expressed in the following *E. coli* strains: the parent *E. coli* strain (Eco1); the *E. coli* strain (Eco2) expressing the Lpl sigma factors; a new strain (Eco3) based on Eco2 expressing the *B. subtilis* rpoD gene from a low copy number plasmid (pETcoco); and a fourth strain (Eco4) based on Eco2 but also expressing both the rpoD and sigB genes from *B. subtilis* from the same low copy number plasmid. Strains Eco1, Eco2, Eco3 and Eco4 will express increasingly more promoters in the order shown from all 3 mpl libraries, as they contain progressively more sigma factors. Eco4 will express more genes from mpl E & mpl B (vs. mpl C), based on the assumption that the first two libraries are enriched for stress responsive genes.

The *B. subtilis* genes can be integrated in the chromosome of the *E. coli*, and then additional sigma factors (e.g., from *clostridia*, which are important soil organisms of major biotechnological importance) can be expressed in order to test if an even larger fraction of metagenomic promoters can be expressed. By expressing a few more sigma factors, the net gain in terms of additional promoters being expressed will decrease. Another avenue is to pursue the use of specialized sigma factors to identify special classes of metagenomic genes/promoters. Mutated libraries of a subset of sigma factors (such as stress sigma factors from Gram$^-$ & Gram$^+$ organisms) aiming to identify one or a few that can recognize the largest set of metagenomic stress-responsive promoters and genes.

Enriching soil microcosms for ethanol and butanol. Soil contains an abundance of prokaryotes that might have enhanced tolerance to stressors such as butanol, ethanol, and other chemicals. Soil will be isolated and enriched with the microbial community for strains that possess higher ethanol or butanol tolerance. Then, the enriched soil will be used for construction of the three metagenomic libraries. To do this, rich garden soil samples of 1-1.5 kg each will be collected and placed in plastic containers with loose lids to generate columns of soil at least 30 cm high aiming to have soil at anaerobic (lower part), microaerobic (near the top) and aerobic (surface). Since *clostridia* have butanol tolerance of up to 1.5% (v/v), and it is desirable to isolate butanol tolerant strains, butanol will be added to two of the soil samples (biological replicates) to a concentration first of 0.75% (to enrich without killing too many organisms), followed at 3 weeks intervals by the addition of butanol at 1.25% (v/v) for a total of ca. 4 months. A large syringe with a long needle will be used to make sure the butanol solution reaches all parts of the column. The same protocol will be followed using 3 & 6% (v/v) (based on reports that *E. coli* can tolerate 6.3% (v/v) ethanol solutions. Two control samples will be left untreated. The 6 soil samples will be stored at room temperature in a well-ventilated space, otherwise undisturbed for 4 months to allow a microbial community to be enriched in tolerant strains.

DNA isolation and library construction. The FastDNA® SPIN kit for Soil (Qbiogene) will be used to isolate metagenomic DNA of ~4-20 kb in size. The soil samples will be homogenized prior to isolating metagenomic DNA aiming to sample cells from the whole column. DNA will be purified to remove impurities using a published protocol. Briefly, NaCl will be added to the DNA sample to adjust the concentration to 0.7 M, followed by addition of specialized NaCl solutions, and the mixture will be incubated at 65° C. for 15 min. Chloroform-isoamyl alcohol will be added to extract the DNA that will then be washed with ethanol and re-suspended in water. The purified DNA will be sheared into small fragments and cloned into our GFP trap (as detailed above; FIG. 1). To assure that the metagenomic library contains DNA of bacteria from a wide range of genera, a 16S RNA phylogenetic classification will be performed. 16S RNA genes will be amplified using primers directed against two highly conserved regions of these genes (Weisburg, Barns et al. 1991). Amplified 16S RNA genes will be cloned (in pCR®8/GW/ TOPO) for sequencing to compare them with the nonredundant sequence NCBI database to validate the diversity of the metagenomic DNA.

EXAMPLE 5

Improved Transcription Enhancement of *L. plantarum* Genes in the Host *E. coli* Through the Expression of *L. plantarum* Sigma Factor rpoD Additional GFP expression profiles were acquired via flow cytometry for strains with and without rpoD over expression containing either the positive control library C5LpSg or the D6LpSg library. All cultures were cultivated in 500 ml baffled flasks containing 100 ml LB with the appropriate antibiotics at 37° C. with shaking at 220 RPM. Cultures were inoculated with 2 ml 15% glycerol LB frozen stock (2% inoculums) and outgrown to early exponential growth phase (optical density between 0.5 and 1) before the expression of the plasmid-based rpoD was induced with 1 mM IPTG. After induction the cultures were monitored by taking optical density measurements and flow samples hourly over the next 7 to 8 hours. Flow samples were prepared by taking 0.5 to 1 ml cell culture, washing the cells twice in 1% NaCl solution and diluting 1-10 µl of the washed cell suspension into a flow tube containing 1 ml 1% NaCl. Samples were then analyzed on a BD FACS ARIA flow cytometer for their green fluorescence originating from GFP.

Figure 5:
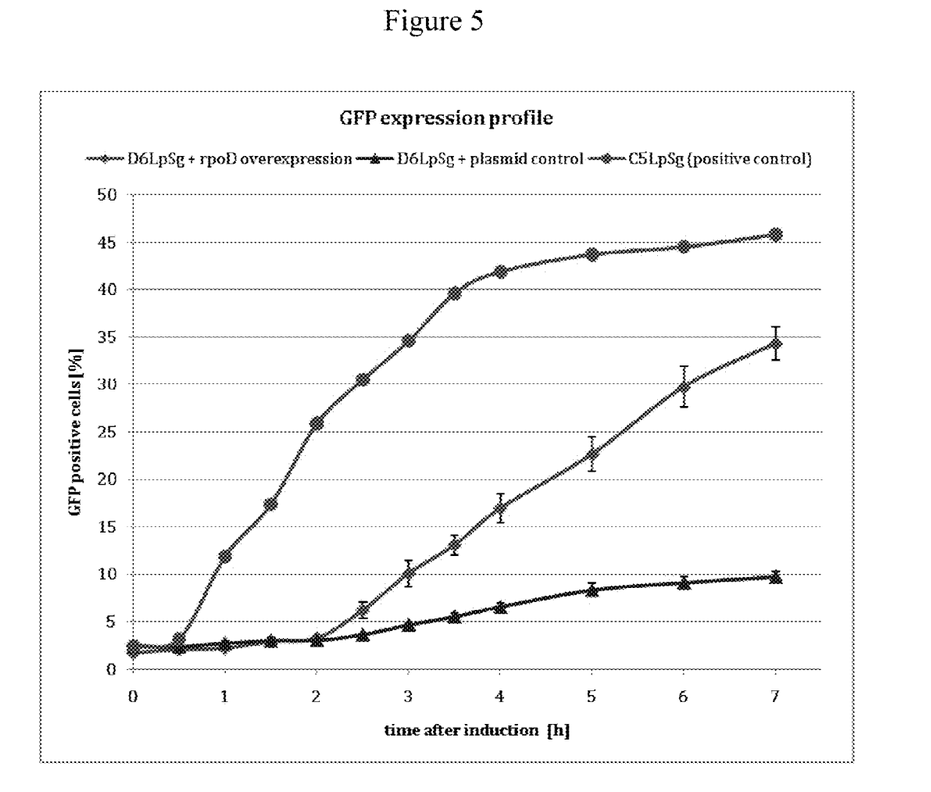
FIG. 5 shows GFP expression profiles of rpoD plasmid based over expression in *E. coli* cells containing the pACYC-rpoD and the D6LpSg (n=3) ( ), *E. coli* cells containing a control plasmid (pAYCY-GUS) and the D6LpSg library (n=3) ( ) and *E. coli* cells containing the C5LpSg library (n=1) ( ). Error bars indicate the standard errors of 3 biological replicates.

As a positive control, the GFP expression profile of *E. coli* cells containing the GFP trap library C5LpSg, which contains an inducible *E. coli* promoter in front of the library inserts, was acquired. The corresponding negative control was acquired as the GFP expression profile of *E. coli* cells containing the GFP trap library D6LpSg, which does not contain any promoter sequence in front of the library insert. These cells also contained a control plasmid, namely pACYC-GUS. This plasmid is identical to the rpoD over expression plasmid pACYC-rpoD containing a promoter-less gus gene instead of the rpoD. Because of the promoter-less insert expression, possible interaction of the gene product can be avoided. The gus gene was chosen to mimic a similar sized control plasmid. In addition, the GFP expression profile of *E. coli* cells containing the rpoD over expression plasmid as well as the D6LpSg library were acquired, and are shown in FIG. 5.

Figure 6:
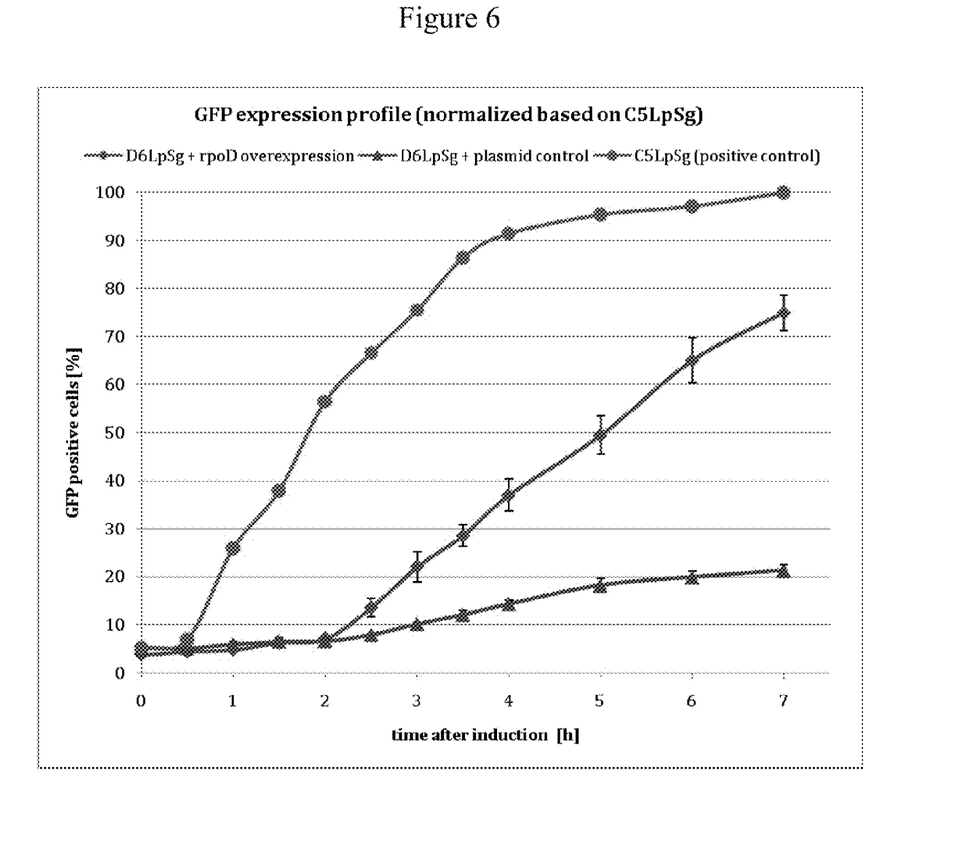
FIG. 6 shows normalized GFP expression profiles of rpoD plasmid based over expression *E. coli* cells containing the pACYC-rpoD and the D6LpSg (n=3) ( ), *E. coli* cells containing a control plasmid (pAYCY-GUS) and the D6LpSg library (n=3) ( ) and *E. coli* cells containing the C5LpSg library (n=1) ( ). The maximum value of the GFP positive population of the positive control (*E. coli* cells containing C5LpSg) was used as a normalization basis and set to 100%. Error bars indicate standard errors of 3 biological replicates.

A normalized GFP expression profile based on the positive control is shown in FIG. 6. Here, the maximum GFP positive cell population of the positive control was used as a normalization basis and set to 100%.

The expression of rpoD leads to an increased GFP positive population in comparison to the plasmid control strain, which indicates that more cells expressing GFP. Since the expression and in particular the transcription of GFP is directly coupled to the transcription of the library insert in the D6LpSg library the increased expression of GFP is due to increased transcription of the library insert. In the presence of the *L. plantarum* sigma factor rpoD, the transcription of library inserts is increased. Since transcription is controlled by the recognition of promoters by the transcription machinery (TM), the augmentation of the native *E. coli* TM with heterologous sigma factors leads to an enhanced recognition of heterologous promoters and transcription enhancement.

EXAMPLE 6

Transcription Enhancement of *L. plantarum* Genes in the Host *E. coli* Through the Expression of Integrated *L. plantarum* Sigma Factor rpoD Chromosomal integration of heterologous genes in a host like *E. coli* provides beneficial properties such as genetic stability as well as eliminates the use of antibiotics to maintain the over expression plasmid. Furthermore, chromosomal integration can solve additional limitations of plasmid based over expression, especially in the context of building a biological alloy with a wide range of heterologous sigma factors. Because it is not necessary to use a selection marker to maintain the chromosomal integration and multiple chromosomal integration can be achieved in the same location as well as in different locations of the chromosome, integration of multiple sigma factors of a wide range of different genera of prokaryotes like *Clostridia*, *Bacillus* or *Streptomyces*, but not limited to these, is possible. Also, sigma factors can be integrated in the same chromosome multiple times to achieve a similar gene dosage as from a multi-copy over expression plasmid. The expression of multiple sigma factors from expression plasmids requires the use of compatible plasmid origin of replication as well as selection markers like antibiotic resistances. Because of the limited availability of these genetic elements the plasmid based over expression of a multitude of heterologous genes is not achievable. Even if several genes are combined in one plasmid, the decreasing transformation efficiency of large plasmids is another limitation, which could not be overcome.

The *L. plantarum* sigma factor rpoD was integrated into the chromosome of the wild-type *E. coli* strain K-12 substrain MG1655 via homologous recombination. As a location for the chromosomal integration, the lac operon was chosen. The rpoD was inserted into the chromosome after the inducible promoter of lacZ. Thus, the expression of the rpoD was again controlled by the lac promoter and could be induced with IPTG. The GFP trap library D6LpSg was introduced into this strain as well as in the wild-type strain K-12 substrain MG1655, which served as a negative control.

Figure 7:
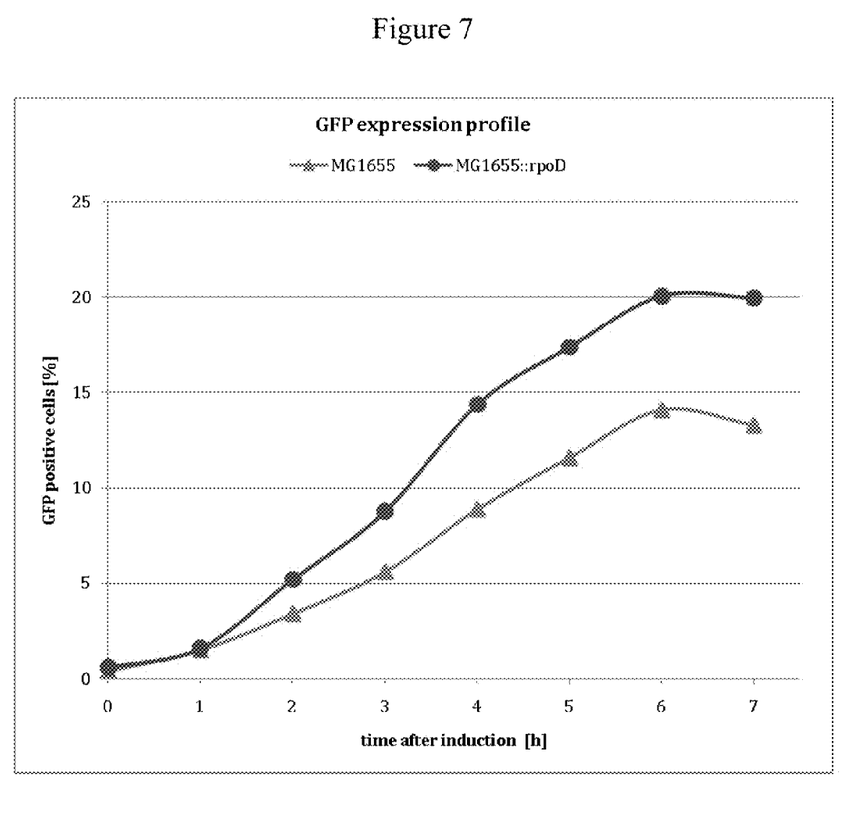
FIG. 7 shows GFP expression profiles of rpoD chromosomal over expression in the rpoD knock-in strain (MG1655:: rpoD) ( ), and wild-type *E. coli* strain transformed with GFP-trap library D6LpSg without any chromosomal modification (MG1655) (negative control) ( ).

The GFP expression profile of these libraries was monitored via flow cytometry for 7 hours after induction. A 100 ml LB culture was inoculated with a 2% glycerol frozen stock and outgrown in 500 ml baffled flask at 37° C. under shaking at 220 RPM to an early exponential growth phase (optical density between 0.5 and 1) before induction with 1 mM IPTG. Hourly optical density measurements were taken to monitor the growth of the culture as well as flow samples to acquire the GFP expression profiles (FIG. 7)

For chromosomal over expression of rpoD, a larger GFP positive population can be observed as for the negative control. The effect of the increased transcription of *L. plantarum* genes present in the library inserts and measured as GFP expression can be observed again as it was for the plasmid based over expression case. Because of the lower gene dosage from chromosomal over expression, the effect is not as great as for the plasmid based over expression. The over expression plasmid pACYC-rpoD has about 14 to 17 copies per cell and a maximum GFP positive population of about 35% was measured via flow cytometry (FIG. 5), whereby only a maximum of about 20% GFP positive cells could be measured for the over expression from the single integration of rpoD into the chromosome (FIG. 7). Nevertheless the chromosomal over expression of rpoD leaded to a larger GFP positive population in comparison to the wild-type strain containing the same GFP-trap library (negative control of FIG. 7), which proves that the chromosomal over expression of sigma factors also leads to an enhanced transcription of heterologous genes in the host *E. coli*.

EXAMPLE 7

Fluorescent Activated Cell Sorting (FACS) on GFP Trap Libraries

In order to reduce the background and false positive events as well as to increase the sensitivity of the method the library D6LpSg present in the wild-type *E. coli* K-12 substrain MG1655 was sorted for GFP negative events. The library was outgrown in 100 ml LB in a 500 ml baffled flask at 37° C. under shaking at 220 RPM. The culture was induced with 1 mM IPTG in exponential growth phase ($OD_{600}$ between 0.5 and 1). The sorting was performed at about 6 hours after induction because this is the time span to achieve the maximum GFP positive cell population (see negative control in FIG. 7). The object of the FACS was to sort for true GFP negative events, so the time point at which the maximum GFP positive population can be observed was chosen in order to sort these events away. Cells that express GFP in the absence of any *L. plantarum* sigma factor represent library inserts with *L. plantarum* promoters, which can be recognized by the native *E. coli* TM.

Figure 8:
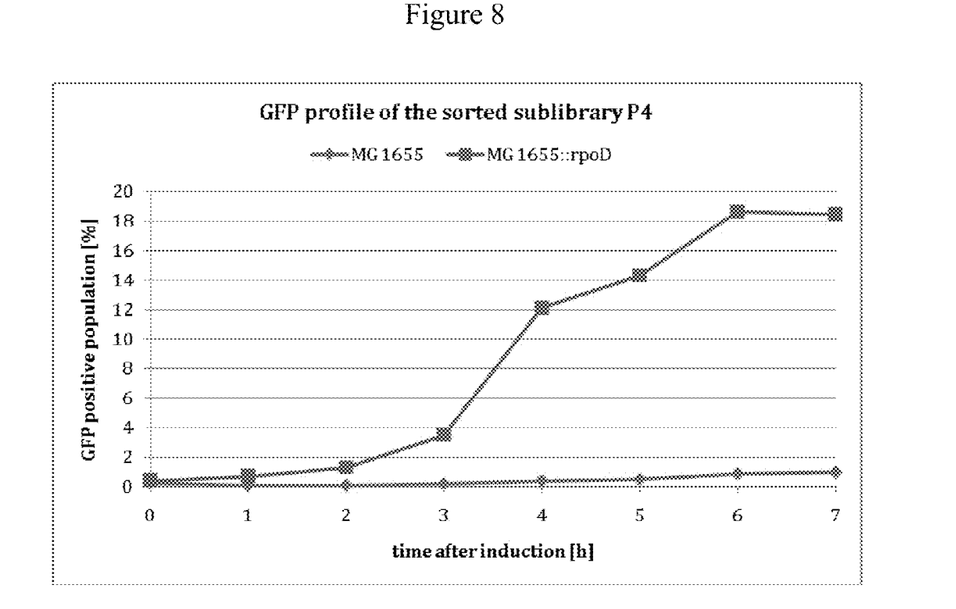
FIG. 8 shows GFP expression profiles of the sorted sublibrary D6LpSg P4 in the rpoD knock-in strain (MG1655:: rpoD) ( ), and the wild-type *E. coli* strain K-12 substrain (MG1655) (negative control) ( ).
Figure 9:
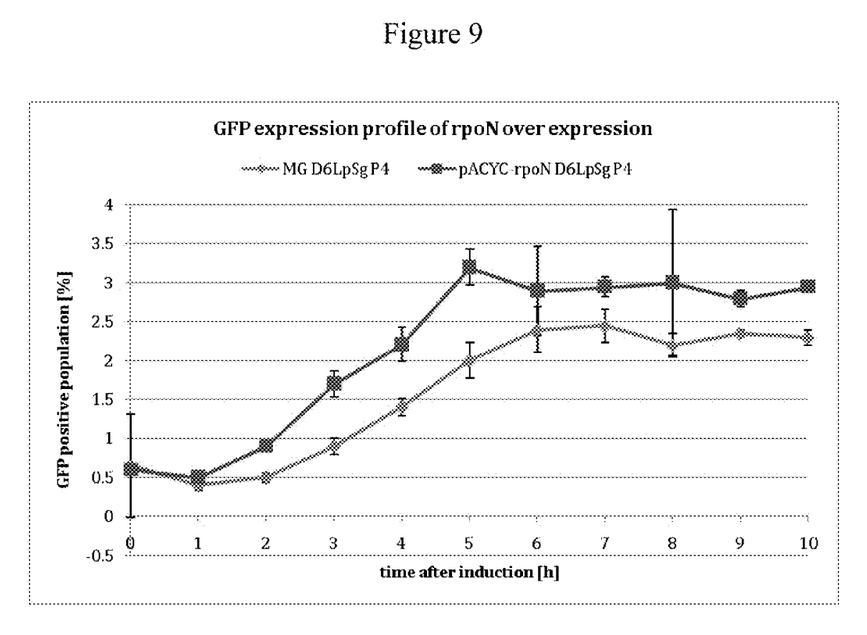
FIG. 9 shows GFP expression profiles of rpoN over expression in the rpoN overexpression strain containing the sublibrary D6LpSg P4 (pACYC-rpoN D6LpSgP4) (n=3) ( ), and wild-type *E. coli* containing the same sublibrary (MG D6LpSgP4) (negative control) (n=3) ( ). Error bars indicate standard errors of 3 biological replicates.

The sorted sublibrary D6LpSg P4 was then introduced into the wild-type *E. coli* strain K-12 substrain MG1655 as well as in the rpoD knock-in strain (MG1655::rpoD). After induction of rpoD, the GFP expression profile was again monitored via flow cytometry (FIG. 8).

The sorted sublibrary D6LpSg P4 does not show any significant GFP positive population in the wild-type strain, which indicates successful sorting of true GFP negative events. The background GFP expression signal originating from library inserts recognized by the native *E. coli* TM was successfully minimized and a true GFP negative sublibrary was created. This sublibrary was then examined for its GFP expression profile in the presence of actively expressed rpoD. The library was introduced into the rpoD knock-in strain and the GFP expression profile was acquired over 7 hours after induction of the rpoD expression with IPTG. The GFP positive population begins to increase after about 2.5 hours and increases to a maximum of about 19%. In the presence of actively expressed rpoD, a fraction of 19% of the cells show a GFP signal indicating that these cells transcribe a *L. plantarum* gene present in the library insert with the help of rpoD. The effect of the augmented TM with the sigma factor rpoD can be reproduced in the sorted sublibary demonstrating that overexpression of rpoD leads to an enhanced transcription of the *L. plantarum* genes in the host *E. coli*.

EXAMPLE 8

Transcription Enhancement of *L. plantarum* Genes in the Host *E. coli* Through the Expression of Additional *L. plantarum* Sigma Factor, Namely rpoN The effect of enhancing the transcription of heterologous genes through the augmentation of the native *E. coli* TM with heterologous sigma factors was further investigated by expressing another sigma factor of *L. plantarum* in the host *E. coli*, namely rpoN. This sigma factor encodes the alternative sigma factor 54, which is involved in stress response. A regulon prediction for rpoN in *L. plantarum* revealed a small regulon size of about 21 genes. Because of this small regulon size, it is expected that only a small fraction of library inserts can be effected by the over expression of this sigma factor. The rpoN was cloned into the pACYC based over expression plasmid and verified by sequencing. Afterwards the rpoN over expression plasmid (pACYC-rpoN) was co-transformed with the sorted sublibrary D6LpSg P4 in the wild-type *E. coli* strain K-12 substrain MG1655 and the GFP expression profile measured via flow cytometry.

The plasmid based over expression of rpoN results in a higher GFP positive population in comparison to a strain not expressing any *L. plantarum* sigma factors (wild-type strain K-12 substrain MG1655). The expression of the sigma factor rpoN also enhances the recognition of *L. plantarum* promoters in the host *E. coli* leading to an increased transcription of library inserts which was measured through the expression of GFP. Thus, the effect of augmenting the native *E. coli* TM with *L. plantarum* sigma factors in order to enhance the transcription of *L. plantarum* genes in the host *E. coli* can be demonstrated for rpoD as well as rpoN, which further demonstrates the generality of the described method. Augmentation of the native *E. coli* TM with heterologous sigma factors can enhance the transcription of heterologous genes, whereby this concept was demonstrated by using sigma factors from the microorganism *L. plantarum*, namely rpoD and rpoN, in conjunction with a *L. plantarum* genomic library.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method for generating a recombinant host *E.coli* bacterium exhibiting a desirable complex phenotype, comprising
    (a) introducing into the host *E. coli* bacterium one or more RNA polymerase subunit genes from a heterologous prokaryote in a genus selected from the group consisting of *Bacillus* and *Lactobacillus*,
    (b) expressing the one or more RNA poly merase subunit genes in the host *E. coli* bacterium;
    (c) introducing into the host *E. coli* bacterium a plurality of function genes from one or more genomic libraries, and
    (d) expressing the plurality of functional genes in the host *E. coli* bacterium, wherein the expression of the plurality of functional genese is enhanced by the expression of the one or more RNA polymerase subunit genes, whereby the host *E. coli* bacterium acquires the desirable complex phenotype.

2. The method of claim 1, further comprising expressing one or more transcript ion factor genes in the host *E.coli* bacterium, wherein the one or more transcription factor genes are derived from the heterologous prokaryote.

3. The method of claim 1, wherein the one or more RNA polymerase subunit genes comprise an alpha, beta, beta', omega or sigma subunit gene.

4. The method of claim 1, wherein the one or more RNA polymerase subunit genes comprise a sigma subunit gene selected from the group consisting of rpoD, rpoN, sigH, rpoS, rpoE, sigB, sigF, sigE, and sigG.

5. The method of claim 1, wherein the one or more genomic libraries are natural or enriched metagenomic libraries.

6. (Previousiy Presented) The method of ciaim 1, wherein the one or more genomic libraries are generated from one or more heterologous prokaryotes.

7. The method of claim 1, wherein the heterologous prokaryote is *Lactobacillus plantarum* or *Bacills subtilis*.

8. The method of claim 1, wherein the one or more RNA polymerase subunit genes are selected from the group consisting of rpoD of *Lactobacillus plantarun*, sigA of *Bacillus subtilis*, and a combination thereof.

* * * * *